(12) United States Patent
Sekula et al.

(10) Patent No.: US 7,563,434 B2
(45) Date of Patent: Jul. 21, 2009

(54) CONSUMER PRODUCT COMPRISING A NATURAL PRESERVATIVE SYSTEM AND A METHOD FOR MAKING THE SAME

(75) Inventors: Bernard Charles Sekula, Glen Gardner, NJ (US); Michael Charles Cirigliano, Cresskill, NJ (US); Monika Maria Tobolewska, Tenafly, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 653 days.

(21) Appl. No.: 11/154,406

(22) Filed: Jun. 16, 2005

(65) Prior Publication Data

US 2006/0286045 A1   Dec. 21, 2006

(51) Int. Cl.
    *A61K 31/26* (2006.01)
(52) U.S. Cl. .................... 424/49; 514/514; 426/638
(58) Field of Classification Search ............... None
    See application file for complete search history.

(56) References Cited

U.S. PATENT DOCUMENTS 6,361,812 B1 * 3/2002 Ekanayake et al. .......... 426/321
6,558,723 B2   5/2003 Ekanayake et al.
2003/0211209 A1   11/2003 Ekanayake et al.
2005/0079255 A1   4/2005 Ekanayake et al.

OTHER PUBLICATIONS

Troncoso et al. Analysis of the isothiocyanates present in cabbage leaves extract and their potential application to control Alternaria rot in bell peppers. Food. Res. Int. 2005;38: 701-708.*
Cook's Illustrated (Mayonnaise-Taste Tests, Mar. 2003).*
Co-pending application for Applicant: Sekula et al., U.S. Appl. No. 11/053,304, filed Feb. 8, 2005.
International Search Report, PCT/EP2006/004888, mailed Aug. 31, 2006, 2 pp.
Eun-Sook Ahn, et al., "Antimicrobial effects of allyl isothiocyanates on several microorganisms", XP002390678, Abstract, Korean Journal of Food Science & Technology, vol. 31, No. 1, 1999, pp. 206-211.

* cited by examiner

*Primary Examiner*—Kamal A Saeed
*Assistant Examiner*—Valerie Rodriguez-Garcia
(74) *Attorney, Agent, or Firm*—Ellen Plotkin

(57) ABSTRACT

Consumer products comprising a natural preservative system are described. The preservative system has a mixture of aliphatic and aromatic isothiocyanates and is suitable for use in a variety of consumer products.

13 Claims, No Drawings

CONSUMER PRODUCT COMPRISING A NATURAL PRESERVATIVE SYSTEM AND A METHOD FOR MAKING THE SAME

FIELD OF THE INVENTION

The present invention is directed to a consumer product comprising a natural preservative system and a method for making the same. More particularly, the present invention is directed to a consumer product comprising a natural preservative system recovered from, for example, mustard seeds wherein the preservative system is suitable for use in products like food products, beverages, health care products and personal care products. In a preferred embodiment, the natural preservative system comprises a mixture of isothiocyanates, and surprisingly, is suitable for use in a variety of consumer products without having a negative impact on flavor and/or performance characteristics of the consumer products. In an especially preferred embodiment, the mixture of isothiocyanates comprises aliphatic isothiocyanate and aromatic isothiocyanate at a concentration ratio from about 1:2 to about 1:25, respectively, and makes up more than about 75 ppm of the total concentration of the consumer product.

BACKGROUND OF THE INVENTION

Preservatives, like sorbate, benzoate and organic acids have been used in food products. Such preservatives offer a degree of microbiological inhibition. However, conventional preservative systems, in order to be effective, require the presence of high levels of organic acids and other microbiological inhibitors in order to ensure microbiological stability. Particularly, standard preservative systems are known to dramatically alter the flavor characteristics of food compositions, rendering the same safe but lacking or unacceptable to consumers from a taste and/or performance standpoint.

Salads, like chilled salads having high levels of protein, are especially difficult to make microbiologically stable. This is true because such salads often have a pH above 4.5 (usually over 5.0) and contain mayonnaise-type products, fats, meats and/or fish as well as water and carbohydrates, thus needing a plethora of antimicrobial agents to render the same safe for human consumption. Moreover, products like real mayonnaise and products made with real mayonnaise are especially difficult to stabilize because only certain preservatives can be used in order to comply with the standard of identity for products labeled as real mayonnaise.

It is of increasing interest to develop a consumer product comprising a natural preservative system that may be used in home and personal care compositions and food and beverage products, and especially, food products that contain an oil-in-water emulsion like real mayonnaise. This invention, therefore, is directed to a consumer product comprising a natural preservative system and a method for making the consumer product. The natural preservative system comprises components derived from, for example, mustard seeds. In a preferred embodiment, the natural preservative system comprises a mixture of isothiocyanates, and surprisingly, is suitable for use in a variety of consumer products without having a negative impact on flavor and product performance characteristics. Such a natural preservative system preferably results in a consumer product with more than about 75 ppm isothiocyanate, based on total concentration of the consumer product, and preferably, comprises a mixture of isothiocyanates comprising aliphatic and aromatic isothiocyanates at a concentration ratio from about 1:2 to about 1:25.

Additional Information

Efforts have been disclosed for making preservative systems. In U.S. Pat. No. 6,361,812, products that may be made with less than about 75 ppm of isothiocyanate compounds and at least one of a sorbate and benzoate are described.

Other efforts have been disclosed for making preservative systems. In U.S. Pat. No. 6,558,723, products that may be made with less than about 75 ppm of isothiocyanate compounds and at least one of a sorbate and benzoate are described.

Still other efforts have been disclosed for making preservative systems. In U.S. Patent Application No. 2003/0211209, products that may be made with less than about 75 ppm of isothiocyanate and at least one of a sorbate and benzoate are described.

None of the additional information describes a consumer product with a natural preservative system and a method for making the consumer product wherein preferably present within the natural preservative system are at least one aliphatic isothiocyanate and at least one aromatic isothiocyanate at a concentration ratio from about 1:2 to about 1:25 and further wherein the natural preservative system makes up more than about 75 ppm of the total concentration of the consumer product it is employed in.

SUMMARY OF THE INVENTION

In a first aspect, the present invention is directed to a microbiologically stable consumer product comprising:

(a) an aliphatic isothiocyanate; and
(b) an aromatic isothiocyanate wherein the aliphatic and aromatic isothiocyantes are present at a concentration ratio from about 1:2 to about 1:25, respectively, and make up collectively, more than about 75 ppm of the total concentration of the consumer product.

In a second aspect, the present invention is directed to a method for making the consumer product of the first aspect of this invention.

Food products, as used herein, mean edible products including but not limited to a filling, dip, sauce, spread, topping, dressing (including light and real mayonnaise products), prepared salads, natural or processed cheese containing food and dairy-based products, and beverages mean, for example, a consumable fluid like tea, coffee, smoothies and juice containing beverages. Dressings, as used herein, are meant to include oil-in-water emulsions and double emulsions, and especially, real mayonnaise. Microbiologically stable (i.e., spoilage free) means no outgrowth of spoilage bacteria, yeast and/or mold and no flavor loss attributable to micro-organism activity for at least about three (3) months before opening at ambient temperature and a pH of less than about 4.75, and at least about one (1) month, and preferably, for at least about one and one-half (1½) months before opening and when kept at about 5° C. and at a pH of less than 5.5, and preferably, less than 5.0. Aromatic isothiocyanate means having a ring with lower pi-election energy from the open chain of the ring and having the group—N═C═S. Aliphatic isothiocyanate means not having an aromatic group and having the group —N═C═S. Substantially free means less than about 0.001% by weight based on total weight of the consumer product. Health care products include skin creams, topical medications and cough syrups and personal care products include soaps, toothpaste, mouthwash, deodorants, shampoos and bathing products. Recovered, as used herein, means obtained by chemically synthesizing or removing from a plant or seeds or flowers (like a plant in the cruciferae species or the seeds or flowers thereof) in isolated form, in a mixture of components, plated on a carrier like a salt or carbohydrate, in oil or as a component of an oil, all of which may be the result of reactions with myrosinase. Natural means produced in nature or synthesized to replicate or be a derivative of a component found in nature.

There is no limitation with respect to the source of the isothiocyanates used in this invention, and it is within the scope of this invention to employ naturally found and synthetically made isothiocyanates that are replicates or derivatives of those found in nature.

In a preferred embodiment, the isothiocyanates are recovered from sources like broccoli, horseradish, mustard, turnip, cabbage, brussel sprouts, kale, collards, cauliflower, cole crops, rutabaga, watercress, radish, nasturtium, spinach, charlock, rapeseed, wasabi, combinations thereof or the like.

Illustrative examples of the types of isothiocyanates suitable for use in this invention include allyl isothiocyanate, 3-butenyl isothiocyanate, benzyl isothiocyanate, 2-butyl isothiocyanate, p-hydroxybenzyl isothiocyanate, methyl isothiocyanate, 4-methylthio-3-butenyl isothiocyanate, 4-pentyl isothiocyanate, 2-phenylethyl isothiocyanate, phenyl isothiocyanate, 6-methylsulfinylhexyl isothiocyanate, 3-methylsulfinylpropyl isothiocyanate, 4-methoxy-3-indolymethyl isothiocyanate, 1-methoxy-3-indolymethyl isothiocyanate, 3-indolylmethyl isothiocyanage, 5-methylthiopentyl isothiocyanate, 2-hydroxy-4-pentenyl isothiocyanate, 4-methylpentyl isothiocyanate, sec-butyl isothiocyanate, 2-hydroxy-3-butenyl isothiocyanate, 3-methylthioalkyl isothiocyanate, mixtures thereof or the like.

Other illustrative non-limiting examples of the isothiocyanates that may be used in this invention are described in U.S. Pat. No. 6,361,812, the disclosure of which is incorporated herein by reference.

In a preferred embodiment, the aliphatic isothiocyanate that is used in this invention is allyl isothiocyanate and the preferred aromatic isothiocyanate is p-hydroxybenzyl isothiocyanate. In a more preferred embodiment, the mixture of isothiocyanates comprises aliphatic isothiocyanate and aromatic isothiocyanate at a concentration ratio from about 1:2 to about 1:20, and in a most preferred embodiment from about 1:3 to about 1:15, including all ranges subsumed therein. In yet another more preferred embodiment, the concentration of isothiocyanate (collectively) in the product is from about 80 ppm to about 400 ppm, and most preferably, from about 80 ppm to about 200 ppm, including all ranges subsumed therein.

The natural preservative system of this invention can be combined with consumer product ingredients to make a product like a food product or combined with product that has already been prepared whereby combined is meant to optionally include marinating. Optionally, the processes may include a heating step. Surprisingly, when using the preservative system of this invention, a product like a filling, dip, sauce, spread, dressing, beverage or the like, is rendered microbiologically safe even when no or substantially no additional and traditional preservative (e.g., sorbate and/or benzoate) is used.

The products of this invention, when food products, typically have a pH below about 6, and preferably, from about 3 to 5.5, and most preferably, from about 3.5 to about 4.5. Moreover, the products of this invention, when food products, are unexpectedly, free of a mustard-like aftertaste. Such food products can optionally comprise meat, fish (e.g., tuna), crustaceans, poultry products, bread crumbs, vegetables (including chunks and puree), protein, wheat, sweeteners (including sugar and artificial sweeteners), oil, emulsions, fruit (including chunks and puree), cheese, nuts, mixtures thereof or the like.

Illustrative and non-limiting examples of preferred food products prepared with the natural preservative system of this invention include water-in-oil and oil-in-water based spreads and toppings, pourable dressings, fruit-based compositions, dressings like mayonnaise and mayonnaise comprising salads like coleslaw, tuna, macaroni, and chicken salad. In a preferred embodiment, the food product made with the natural preservative system of this invention is a real mayonnaise comprising 65% by weight oil or more and less than about 82% by weight oil, and most preferably, from 65% to about 75% by weight oil. In an especially preferred embodiment, the food product is mayonnaise comprising about from 66% to about 72% by weight oil based on total weight of the food product and including all ranges subsumed therein.

Also, the food product of this invention can optionally comprise soluble fibers, insoluble fibers (like citrus fibers), gums (like xanthan), starches, cellulose, vitamins, buffers, antioxidants, preservatives (like sorbates and benzoates, lauramide of arginine monohydrochloride (LAE), nisin, natamycin, benzoic acid, coumaric acid, salicylic acid, vanillic acid, caffeic acid, cinnamic acid, ferulic acid, lactic acid, acetic acid, adipic acid, derivatives thereof, salts thereof, mixtures thereof and the like), colorants, acidulants (including inorganic acids), emulsifiers, alcohol, spices (including salt), syrups, milk, food grade dispersants or stabilizers (like propylene glycol alginate), solubilizing agents (like propylene glycol), milk powder or mixtures thereof.

An often preferred food product of this invention preferably comprise at least about 30% by weight meat, and most preferably, from about 45 to about 65% by weight meat and from about 0.0 to about 15% by weight solid particulate like vegetables and/or fruit.

The packaging suitable for use with the food products made according to this invention is often a glass jar, food grade sachet, a plastic tub or squeezable plastic bottle. Sachets are preferred for food service applications, a tub is preferred for spreads and protein based salads, and a squeezable plastic bottle is often preferred for non-spreads and domestic use.

The following examples are provided to illustrate an understanding of the present invention. The examples are not intended to limit the scope of the claims.

EXAMPLE 1

Real mayonnaise compositions having about 70% by weight oil and about 50 ppm of allyl isothiocyanate were made. No aromatic isothiocyanate was incorporated. Stability studies of the same demonstrated that subsequent to the yeast counts being reduced to non-detectable levels by week 6, a two log increase in yeast counts occurred between weeks 6 and 12 at ambient temperature. The initial inoculum was about 10,000 cfu/gram.

EXAMPLE 2

Mayonnaise compositions similar to the ones described in Example 1 were made except that about 50 pm allyl isothiocyanate and about 100 ppm of 4-hydrozybenzyl isothiocyanate were used as preservative. Stability studies demonstrated that after about 12 weeks at ambient temperature, there was no yeast or bacteria outgrowth at all initial levels of inoculum.

Surprisingly, real mayonnaise compositions made with the preservative systems of the present invention were stable, notwithstanding the fact that they were formulated with about 7% more water than conventional mayonnaise compositions. Also, and surprisingly, a skilled group of about 10 panelists concluded that the reduced oil mayonnaise compositions formulated with the preservative system of this invention were free of a mustard-like aftertaste.

What is claimed is:

1. A microbiologically stable consumer product comprising a preservative system comprising:
    (a) an aliphatic isothiocyanate; and
    (b) an aromatic isothiocyanate;
wherein the aliphatic and aromatic isothiocyanates are present at a concentration ratio from about 1:2 to about 1:25, respectively, and make up collectively, more than about 75 ppm of the total concentration of the consumer; and
    wherein said stable consumer product is a food or beverage comprising water and oil.

2. The microbiologically stable consumer product according to claim 1 wherein the aliphatic and aromatic isothiocyanates are present at a concentration ratio from about 1:2 to about 1:20, respectively.

3. The microbiologically stable consumer product according to claim 1 wherein the aliphatic and aromatic isothiocyanates are present at a concentration ratio from about 1:3 to about 1:15, respectively.

4. The microbiologically stable consumer product according to claim 1 wherein the aliphatic and aromatic isothiocyanates, collectively, make up from about 80 to about 400 ppm of the total concentration of the consumer product.

5. The microbiologically stable consumer product according to claim 1 wherein the aliphatic and aromatic isothiocyanates, collectively, make up from about 80 to about 200 ppm of the total concentration of the consumer product.

6. The microbiologically stable consumer product according to claim 1 wherein the consumer product is a filling, dip, sauce, spread, topping, dressing, prepared salad, cheese product, dairy-based product or beverage.

7. The microbiologically stable consumer product according to claim 1 wherein the consumer product is mayonnaise comprising 65 to less than about 82% by weight oil.

8. The microbiologically stable consumer product according to claim 1 wherein the consumer product is mayonnaise comprising from about 65% to about 75% by weight oil.

9. The microbiologically stable consumer product according to claim 1 wherein the consumer product comprises from about 66% to about 72% by weight oil.

10. The microbiologically stable consumer product according to claim 1 wherein the food product is free of a mustard-like aftertaste.

11. The microbiologically stable consumer product according to claim 1 wherein the food product has a pH of less than about 6.

12. The microbiologically stable consumer product according to claim 1 wherein the food product has substantially no additional preservative in addition to the aliphatic and aromatic isothiocyanates.

13. The microbiologically stable consumer product according to claim 1 wherein the food product demonstrates no yeast or bacteria outgrowth.

* * * * *